US012805929B2

(12) United States Patent
Balkovec et al.

(10) Patent No.: US 12,805,929 B2
(45) Date of Patent: Nov. 24, 2026

(54) SYSTEM AND METHOD FOR PERICARDIAL PUNCTURE

(71) Applicant: Boston Scientific Medical Device Limited, Galway (IE)

(72) Inventors: Christian Balkovec, Burlington (CA); Gareth Davies, Toronto (CA); Matthew DiCicco, Guelph (CA); Eduardo Moriyama, Richmond (CA)

(73) Assignee: Boston Scientific Medical Device Limited, Galway (IE)

( * ) Notice: Subject to any disclaimer, the term of this patent is extended or adjusted under 35 U.S.C. 154(b) by 521 days.

(21) Appl. No.: 18/155,478

(22) Filed: Jan. 17, 2023

(65) Prior Publication Data

US 2023/0149076 A1 May 18, 2023

Related U.S. Application Data

(63) Continuation of application No. PCT/IB2021/056368, filed on Jul. 14, 2021.

(Continued)

(51) Int. Cl.
*A61B 18/00* (2006.01)
*A61B 18/14* (2006.01)

(Continued)

(52) U.S. Cl.
CPC .......... *A61B 18/1492* (2013.01); *A61N 1/362* (2013.01); *A61B 17/00234* (2013.01);

(Continued)

(58) Field of Classification Search
CPC .......... A61B 1/362; A61B 2017/00247; A61B 2018/00363; A61B 2018/00994
See application file for complete search history.

(56) References Cited

U.S. PATENT DOCUMENTS 6,006,134 A * 12/1999 Hill .................... A61B 17/3417 607/9
2002/0019623 A1* 2/2002 Altman ............. A61M 25/0084 604/20

(Continued)

FOREIGN PATENT DOCUMENTS

| | | | |
|---|---|---|---|
| EP | 1750804 | A1 | 2/2007 |
| EP | 3636177 | A1 | 4/2020 |
| WO | 2019215618 | A1 | 11/2019 |

OTHER PUBLICATIONS

Volpe JK, Makaryus AN. Anatomy, Thorax, Heart and Pericardial Cavity. [Updated Jul. 25, 2023]. In: StatPearls [Internet]. Treasure Island (FL): StatPearls Publishing; Jan. 2025. Available from: https://www.ncbi.nlm.nih.gov/books/NBK482452/ (Year: 2023).*

(Continued)

*Primary Examiner* — Jaymi E Della
(74) *Attorney, Agent, or Firm* — Nelson Mullins Riley & Scarborough LLP

(57) ABSTRACT

A method for pericardial puncture includes contacting a pericardium of a heart of a patient with an electrode of a medical device, and while the heart is in a contracted state, delivering radiofrequency energy from the electrode to puncture the pericardium. A stimulus signal can be delivered to the heart to force contraction and transient standstill of the heart in the contracted state. Electrocardiography monitoring and/or medical imaging can be used to determine when the heart is in the contracted state.

13 Claims, 2 Drawing Sheets

Related U.S. Application Data

(60) Provisional application No. 63/052,999, filed on Jul. 17, 2020.

(51) Int. Cl.
*A61N 1/362* (2006.01)
*A61B 17/00* (2006.01)

(52) U.S. Cl.
CPC ............... *A61B 2017/00247* (2013.01); *A61B 2018/00363* (2013.01); *A61B 2018/00839* (2013.01); *A61B 2018/00994* (2013.01)

(56) References Cited

U.S. PATENT DOCUMENTS

| | | | | |
|---|---|---|---|---|
| 2014/0228841 | A1* | 8/2014 | Davies | A61B 17/3478 606/45 |
| 2015/0182740 | A1 | 7/2015 | Mickelsen | |
| 2016/0066989 | A1* | 3/2016 | Davies | A61B 18/1492 606/41 |
| 2016/0175009 | A1* | 6/2016 | Davies | A61B 17/3478 606/191 |
| 2016/0184595 | A1* | 6/2016 | Hossainy | A61M 39/0247 607/116 |
| 2017/0296217 | A1* | 10/2017 | Hissong | A61N 7/022 |
| 2018/0303543 | A1 | 10/2018 | Stewart et al. | |

OTHER PUBLICATIONS

International Search Report for PCT Application No. PCT/IB2021/056368 mailed Oct. 15, 2021.

Extended European Search Report for International Patent Application No. PCT/IB2021/056368 mailed Jul. 17, 2024. 7 pages.

* cited by examiner

SYSTEM AND METHOD FOR PERICARDIAL PUNCTURE

CROSS REFERENCE TO RELATED APPLICATION

This application is a continuation application of International Application No. PCT/162021/056368, filed Jul. 14, 2021, titled "SYSTEM AND METHOD FOR PERICARDIAL PUNCTURE," which claims priority to U.S. Provisional Application No. 63/052,999, filed Jul. 17, 2020, titled "SYSTEM AND METHOD FOR PERICARDIAL PUNCTURE," the entire disclosures of which are incorporated herein by reference.

FIELD

This document relates to methods for carrying out medical procedures. More specifically, this document relates to methods for pericardial puncture, and related systems.

SUMMARY

The following summary is intended to introduce the reader to various aspects of the detailed description, but not to define or delimit any invention.

Methods for pericardial puncture are disclosed. According to some aspects, a method for pericardial puncture includes: a. contacting a pericardium of a heart of a patient with an electrode of a medical device; and b. while the heart is in a contracted state, delivering radiofrequency energy from the electrode to puncture the pericardium.

The method can further include, prior to step b., delivering a stimulus signal to the heart to force contraction and transient standstill of the heart in the contracted state.

The stimulus signal can be delivered from a pulse generator to the electrode of the medical device. The radiofrequency energy can be delivered from a radiofrequency generator to the electrode. The delivery of radiofrequency energy from the radiofrequency generator can be automatic based on the delivery of the stimulus signal and can occur automatically following the delivery of the stimulus signal. The pulse generator can communicate with the radiofrequency generator to coordinate the delivery of the stimulus signal and the delivery of the radiofrequency energy.

In some examples, the stimulus signal is delivered from the electrode of the medical device.

In some examples, the stimulus signal is delivered from a secondary medical device. During delivery of the stimulus signal, the secondary medical device can be spaced from the heart. The method can further include, prior to step a., advancing the electrode towards the heart via an introducer, and the stimulus signal can be delivered from the introducer to the heart.

In some examples, step a. can include applying force to the heart with the electrode. Delivering a stimulus signal to the heart can cause the heart to move away from the electrode to reduce the amount of force applied to the heart with the electrode.

In some examples, the method further includes, prior to step b., using electrocardiography monitoring to determine when the heart is in the contracted state.

In some examples, the method further includes, prior to step b., using medical imaging to determine when the heart is in the contracted state.

Systems of medical devices are also disclosed. According to some aspects, a system of medical devices includes a pulse generator for delivering a stimulus signal, a radiofrequency (RF) generator for delivering RF energy, and a medical device. The medical device includes an elongate shaft and an electrode at a distal end of the shaft. The electrode is electrically connected to the pulse generator for receiving a stimulus signal from the pulse generator and delivering the stimulus signal to a heart to force contraction and transient standstill of the heart. The electrode is electrically connected to the RF generator for receiving RF energy from the RF generator and delivering the RF energy to a tissue of the heart to puncture the tissue.

In some examples, the RF generator is in communication with the pulse generator for coordination of the delivery of the stimulus signal and the RF energy.

In some examples, the elongate shaft includes a wire and a layer of electrical insulation on the wire. The electrode can include an electrically exposed end of the wire. The elongate shaft can be flexible or stiff.

In some examples, the system further includes an introducer through which the medical device is advanceable.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein is a method for pericardial puncture in which puncture occurs while the heart is in a contracted state (i.e. during systole). For example, a stimulus signal can be delivered to the heart to force contraction and transient standstill of the heart in the contracted state. Then, while the heart is in the contracted state, radiofrequency (RF) energy can be delivered to puncture the pericardium. Alternatively, ECG monitoring can be used to determine when the heart is naturally in a contracted state, and while the heart is naturally in the contracted state, radiofrequency (RF) energy can be delivered to puncture the pericardium. Puncturing the pericardium while the heart is in a contracted state can reduce the risk of puncturing deeper tissue within the heart (e.g. the myocardium) and can thus enhance patient safety. More specifically, when using an RF puncture device to puncture the pericardium, the force applied to the heart by the device will vary during beating of the heart. That is, during diastole, the heart will move towards the RF puncture device, increasing the force applied to the heart by the device. In contrast, during systole, the heart will move away from the RF puncture device, decreasing the force applied to the heart by the device. Because the heart moves away from the RF puncture device during systole and the force applied to the heart by the RF puncture device is decreased during systole, puncturing the pericardium during systole can minimize the depth to which the RF puncture device penetrates into the heart (as compared to puncturing during diastole).

Figure 1:
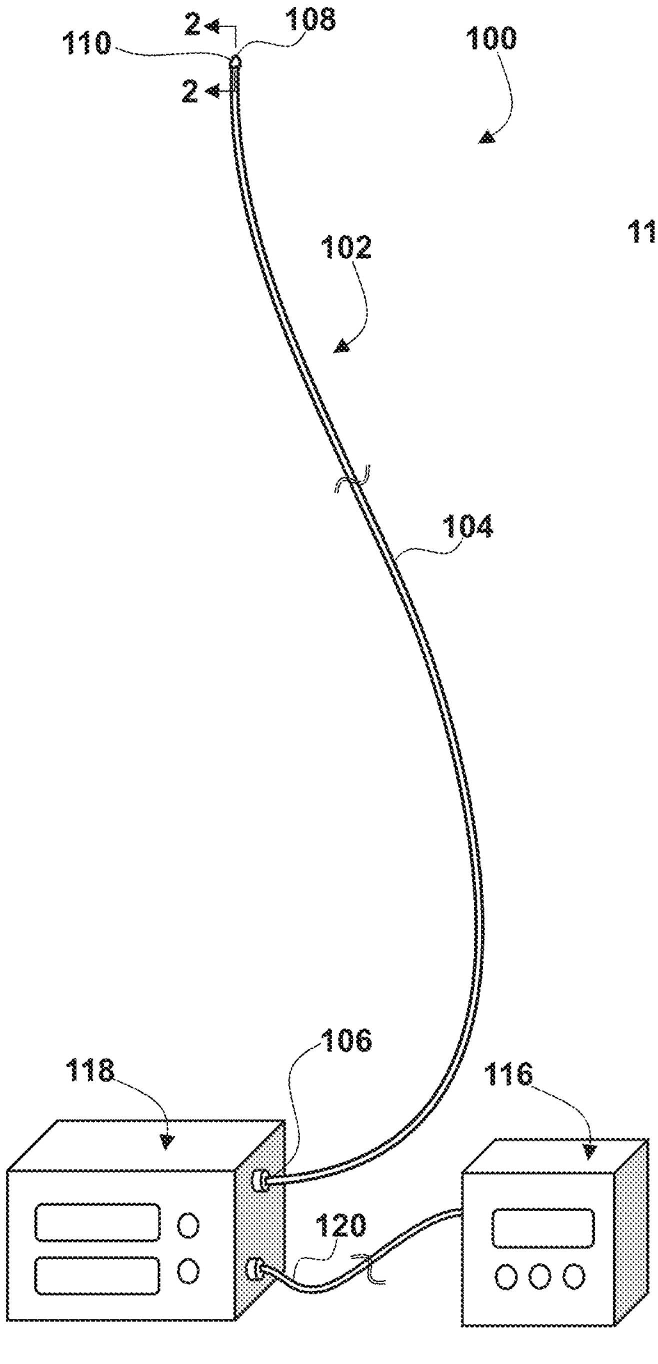
FIG. 1 is a perspective view of a system for pericardial puncture.
Figure 2:
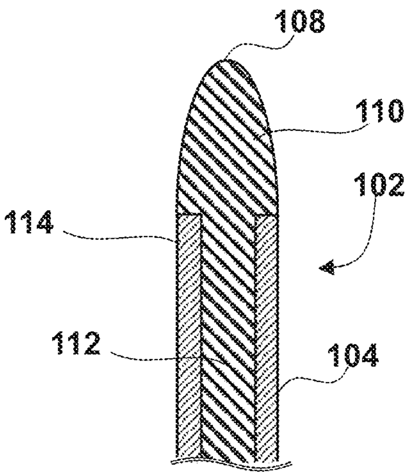
FIG. 2 is a cross section taken along line 2-2 in FIG. 1.

Referring now to FIG. 1, an example system 100 of medical devices is shown. The system 100 generally includes a medical device 102 that can be used for both RF puncture and stimulus signal delivery, and that can also be used as a guidewire. More specifically, the medical device 102 includes an elongate shaft 104 having a proximal end 106 and a distal end 108. An electrode 110 is at the distal end 108. Referring to FIG. 2, in the example shown, the shaft 104 includes a wire 112 and a layer of electrical insulation 114 on the wire 112, and the electrode 110 is in the form of an electrically exposed end of the wire 112. The electrode 110 can deliver a stimulus signal to a tissue and deliver RF energy to puncture the tissue, as will be described below.

In the example shown, the shaft 104 is resiliently flexible. That is, the shaft 104 is biased towards a generally straight configuration, but can be curved or bent with the application of force. When force is removed, the shaft 104 will move back towards a straight configuration.

In alternative examples, the shaft can be relatively stiff (e.g. the shaft can be of a similar stiffness to a needle).

Referring back to FIG. 1, the system 100 further includes a pulse generator 116 and an RF generator 118, and the electrode 110 is electrically connected to the pulse generator 116 and the RF generator 118 via the wire 112 (not shown in FIG. 1).

The pulse generator 116 can generate a stimulus signal, and the electrode 110 can receive the stimulus signal and deliver the stimulus signal to a tissue with which the electrode 110 is in contact (e.g. the pericardium). When delivered to the heart, the stimulus signal can force contraction and transient standstill of the heart in a contracted state (e.g. the stimulus signal can be a rapid pacing signal). The pulse generator 116 can be, for example, one sold by GE Healthcare under the brand name Micropace.

The RF generator 118 can generate RF energy and the electrode 110 can receive the RF energy from the RF generator 118 and deliver the RF energy to the tissue with which the electrode 110 is in contact (e.g. the pericardium). When delivered to the tissue, the RF energy can cause puncture of the tissue. The RF generator 118 can be, for example, one sold by Baylis Medical Company Inc. (Montreal, Canada). The RF generator 118 can be connected to one or more grounding pads (not shown).

Referring still to FIG. 1, in the example shown, the medical device 102 is directly electrically connected to the RF generator 118 at the proximal end 106 of the shaft 104, and the RF generator 118 is electrically connected to the pulse generator 116 by a cable 120, so that the medical device 102 is indirectly electrically connected to the pulse generator 116 via the RF generator 118. As will be described below, electrically connecting the RF generator 118 and the pulse generator 116 allows for communication between the RF generator 118 and the pulse generator 116, so that delivery of the stimulus signal and the delivery of RF energy can be coordinated. In alternative examples, the medical device 102 can be directly electrically connected to both the RF generator 118 and the pulse generator 116, or indirectly electrically connected to both the RF generator 118 and the pulse generator 116 (e.g. via an accessory device), or directly electrically connected to the pulse generator 116 and indirectly electrically connected to the RF generator 118 via the pulse generator 118.

Figure 3:
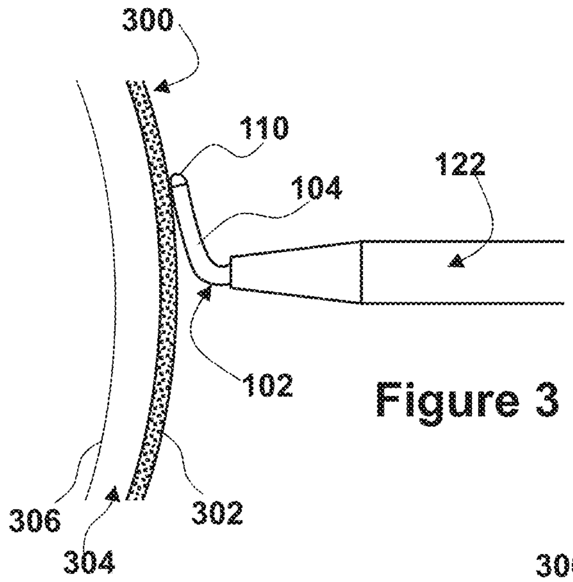
FIG. 3 is a schematic view showing a step of a method for pericardial puncture.
Figure 4:
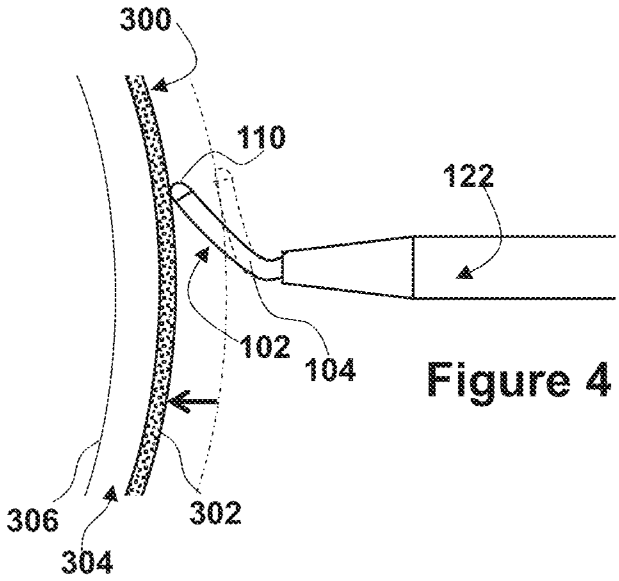
FIG. 4 is a schematic view showing a step subsequent to that of FIG. 3.
Figure 5:
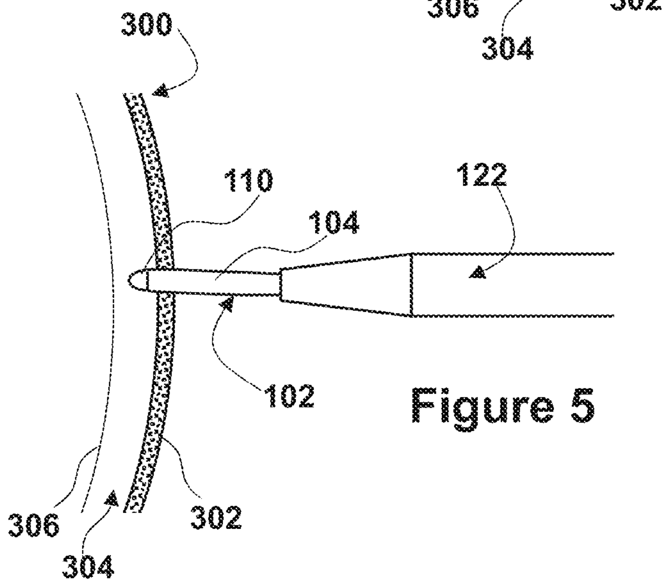
FIG. 5 is a schematic view showing a step subsequent to that of FIG. 4.

Referring now to FIGS. 3 to 5, a method of puncturing the pericardium will be described. The method will be described with reference to the system 100 and medical device 102 of FIGS. 1 and 2; however, the method is not limited to the system 100 and/or the medical device 102, and the system 100 and medical device 102 are not limited to operation according to the method. In FIGS. 3 to 5, the heart is generally shown at 300, with the pericardium generally shown at 302, the pericardial space generally shown at 304, and the myocardium generally shown at 306.

Referring first to FIG. 3, in use, the medical device 102 can be advanced towards a target location of the pericardium 302. The medical device 102 can optionally be advanced towards the pericardium via an introducer 122. For example, the introducer 122 can be percutaneously advanced towards the target location via the subxiphoid approach, with a stylet (not shown) received in the introducer 122. The stylet can then be removed, and the medical device 102 can be advanced through the introducer 122 towards the target location, to contact the pericardium with the electrode 110. In FIG. 3, the heart is shown in diastole, and the medical device 102 has been advanced slightly beyond the minimum distance needed to contact the pericardium 302 when the heart 300 is in diastole, so that contact with the pericardium 302 causes the shaft 104 to flex away from a straight configuration. Due to the resiliently flexible nature of the shaft 104 and the bias of the shaft 104 towards a straight configuration, when in the configuration shown in FIG. 3, the shaft 104 will apply force to the pericardium 302.

Once the electrode 110 is in contact with the pericardium 302 and in the position shown in FIG. 3, a stimulus signal can be delivered from the pulse generator 116 (not shown in FIGS. 3 to 5) to the electrode 110, and from the electrode 110 to the heart 300. The stimulus signal can be tuned so that it forces contraction and transient standstill of the heart 300 in a contracted state (i.e. in systole), as shown in FIG. 4. For example, the stimulus signal can be a rapid pacing signal. Due to the resiliently flexible nature of the shaft 104, the shaft 104 will remain in contact with the heart 300 as the heart 300 contracts and the shaft 104 straightens slightly. However, due to the contraction of the heart 300, the heart 300 will move away from the medical device 102 and the force applied to pericardium 302 by the medical device 102 when in the configuration shown in FIG. 4 will be less than the force applied to pericardium 302 by the medical device 102 when in the configuration shown in FIG. 3. In FIG. 4, the former position of the pericardium 302 and the medical device 102 is shown in dotted line.

While the heart 300 and medical device 102 are in the configuration shown in FIG. 4 (i.e. while the heart 300 is in the contracted state and while the electrode 110 is in contact with the heart 300), RF energy can be delivered from the RF generator 118 (not shown in FIGS. 3 to 5) to the electrode 110, and from the electrode 110 to the pericardium 302, to puncture the pericardium 302. As mentioned above, in order to ensure that RF energy is delivered while the heart 300 and medical device 102 are in the configuration shown in FIG. 4, the pulse generator 116 and the RF generator 118 are in communication, to coordinate delivery of the stimulus signal and delivery of the RF energy. For example, the delivery of RF energy can be automatic, based on the delivery of the stimulus signal. More specifically, the RF generator 118 can be configured to deliver RF energy automatically, either immediately following the delivery of the stimulus signal, or after a set time period has passed following the delivery of the stimulus signal, to ensure that RF energy is delivered only when the heart 300 is forced into transient standstill in the contracted state. Delivery of RF energy to the heart 300 when the heart 300 and the medical device 102 are in the configuration shown in FIG. 4 can cause the electrode 110 to puncture the pericardium 302, as shown in FIG. 5. Delivery of RF energy can be brief (e.g. lasting less than one second) and can be stopped as soon as puncture has occurred. Because puncture occurs when the heart 300 is in the contracted state, the medical device 102 penetrates only a small amount into the pericardial space 304, and does not puncture or damage the myocardium 306.

After the pericardium 302 has been punctured and after the delivery of RF energy has been stopped, the medical device 102 can be further advanced into the pericardial space 304, and can be used as a guidewire in further steps of the medical procedure.

In the example described above, the pulse generator 116 is electrically connected to the medical device 102, and the stimulus signal is delivered from the pulse generator to the electrode 110 and from the electrode 110 to the heart 300. In alternative examples, a secondary medical device can be electrically connected to the pulse generator 116, and the stimulus signal can be delivered from the secondary medical device to the heart 300. Furthermore, the secondary medical device may be spaced from the heart 300 during delivery of the stimulus signal (i.e. the secondary medical device need not be in contact with the heart 300). For example, the introducer 122 can include a stimulus electrode and can be electrically connected to the pulse generator 116, and the stimulus signal can be delivered from the stimulus electrode of the introducer 122 to the heart 300.

In the example described above, in order to ensure or facilitate delivery of RF energy when the heart 300 is in the contracted state, the heart 300 is forced into the contracted state by delivery of a stimulus signal. In alternative examples, delivery of a stimulus signal can be omitted, and delivery of RF energy can be coordinated with the natural rhythm of the heart. For example, medical imaging (e.g. fluoroscopy, ultrasound, and/or echocardiography) and/or electrocardiography (ECG) monitoring can be used to determine when the heart 300 is in a contracted state and/or to predict when the heart 300 will be in a contracted state. In the case of ECG monitoring, the ECG monitoring can optionally be done via the medical device 102—i.e. the electrode 110 can also serve as an ECG electrode, and can receive ECG signals from the heart 300 and deliver the ECG signals to an ECG monitoring system (not shown). The ECG monitoring system can optionally be in communication with the RF generator 118, in order to coordinate delivery of RF energy with ECG monitoring, and delivery of RF energy can be automatic based on the ECG signals received from the heart 300. More specifically, delivery of RF energy can optionally occur automatically when the ECG monitoring system determines that the heart 300 is contracted. For example, the ECG monitoring system can detect the beginning of the RR interval in the heart 300, and the RF generator 118 can automatically deliver RF energy at the beginning of the RR interval (e.g. for up to 0.4 seconds, or for between 0.1 and 0.4 seconds). Alternatively, a user can read the ECG monitoring system to determine that the heart 300 is contracted, and manually initiate delivery of RF energy.

In examples wherein ECG monitoring is used to determine or predict when the heart 300 is in a contracted state, the ECG monitoring system can be configured to distinguish isovolumetric contraction, ejection, isovolumetric relaxation, rapid inflow, diastasis, and atrial systole.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method for pericardial puncture, comprising:

a. contacting a pericardium of a heart of a patient with an electrode of a medical device, the electrode located at a distal end of an elongate shaft that is resiliently flexible and is biased towards a straight profile, wherein the elongate shaft exhibits a first deflection profile against the pericardium during the contacting;

b. delivering, with the electrode, a stimulus signal to the pericardium of the heart to force contraction and transient standstill of the heart in a contracted state, wherein the elongate shaft exhibits a second deflection profile against the pericardium that is lesser than the first deflection profile during the delivering of the stimulus signal;

c. while the heart is in the contracted state, delivering radiofrequency energy from the electrode to puncture the pericardium and to penetrate into pericardial space between the pericardium and myocardium with the electrode; and d. advancing the elongate shaft into the pericardial space, wherein the elongate shaft at least partially returns to the biased straight profile after penetration.

2. The method of claim 1, wherein the stimulus signal is delivered from a pulse generator to the electrode of the medical device.

3. The method of claim 2, wherein the radiofrequency energy is delivered from a radiofrequency generator to the electrode of the medical device.

4. The method of claim 3, wherein the delivery of radiofrequency energy from the radiofrequency generator is automatic based on the delivery of the stimulus signal.

5. The method of claim 4, wherein the delivery of radiofrequency energy occurs automatically after a set time period has passed following the delivery of the stimulus signal.

6. The method of claim 5, wherein the pulse generator communicates with the radiofrequency generator to coordinate the delivery of the stimulus signal and the delivery of the radiofrequency energy.

7. The method of claim 1, wherein step a. comprises applying force to the heart with the electrode; and delivering the stimulus signal to the heart causes the heart to move away from the electrode to reduce an amount of the force applied to the heart with the electrode.

8. The method of claim 1, further comprising:

prior to step c., using electrocardiography monitoring to determine when the heart is in the contracted state.

9. The method of claim 1, further comprising using medical imaging to determine when the heart is in the contracted state.

10. A system of medical devices, comprising:

a pulse generator for delivering a stimulus signal;

a radiofrequency (RF) generator for delivering RF energy; and a medical device comprising an elongate shaft that is resiliently flexible and biased towards a straight profile and an electrode at a distal end of the elongate shaft, wherein the electrode is electrically connected to the pulse generator to receive and deliver the stimulus signal from the pulse generator to a pericardium of a heart to induce contraction and transient standstill of the heart;

wherein the elongate shaft is configured to exhibit a first deflection profile against the pericardium during contact prior to the delivery of the stimulus signal and a second deflection profile that is lesser than the first deflection profile during the delivery of the stimulus signal;

wherein the electrode is electrically connected to the RF generator to receive and deliver RF energy from the RF generator to the pericardium while the heart is in the contracted state to puncture the pericardium and penetrate into a pericardial space between the pericardium and myocardium with the electrode; and wherein the elongate shaft is configured to be advanced into the pericardial space following puncture and at least partially return to the biased straight profile after penetration.

11. The system of claim 10, wherein the RF generator is in communication with the pulse generator for coordination of the delivery of the stimulus signal and the RF energy.

12. The system of claim 10, wherein the elongate shaft comprises a wire and a layer of electrical insulation on the wire.

13. The system of claim 12, wherein the electrode comprises an electrically exposed end of the wire.

* * * * *